United States Patent [19]
Doyle

[11] Patent Number: 6,029,946
[45] Date of Patent: Feb. 29, 2000

[54] NEEDLELESS VALVE

[75] Inventor: Mark Christopher Doyle, San Diego, Calif.

[73] Assignee: Tiva Medical Inc., Carlsbad, Calif.

[21] Appl. No.: 08/929,919

[22] Filed: Sep. 15, 1997

[51] Int. Cl.$^7$ .................................................. A61M 5/00
[52] U.S. Cl. ........................ 251/149.1; 604/249; 604/256
[58] Field of Search .............................. 251/149.1, 149.6, 251/118; 604/249, 256

[56] References Cited

U.S. PATENT DOCUMENTS

| Re. 33,925 | 5/1992 | Bonaldo . |
|---|---|---|
| Re. 34,223 | 4/1993 | Bonaldo . |
| Re. 35,539 | 6/1997 | Bonaldo . |
| 3,127,892 | 4/1964 | Bellamy, Jr. et al. . |
| 3,304,047 | 2/1967 | Martin ...................................... 251/118 |
| 3,334,860 | 8/1967 | Bolton, Jr. ............................ 251/149.1 |
| 3,986,508 | 10/1976 | Barrington . |
| 4,066,067 | 1/1978 | Micheli . |
| 4,080,965 | 3/1978 | Phillips . |
| 4,121,585 | 10/1978 | Becker, Jr. . |
| 4,133,441 | 1/1979 | Mittleman et al. . |
| 4,195,632 | 4/1980 | Parker et al. . |
| 4,340,049 | 7/1982 | Munsch . |
| 4,387,879 | 6/1983 | Tauschinski . |
| 4,397,442 | 8/1983 | Larkin . |
| 4,457,749 | 7/1984 | Bellotti et al. . |
| 4,511,359 | 4/1985 | Vaillancourt . |
| 4,623,332 | 11/1986 | Lindmayer et al. . |
| 4,662,878 | 5/1987 | Lindmayer . |
| 4,723,603 | 2/1988 | Plummer . |
| 4,774,964 | 10/1988 | Bonaldo . |
| 4,774,965 | 10/1988 | Rodriguez et al. . |
| 4,781,702 | 11/1988 | Herrli . |
| 4,816,024 | 3/1989 | Sitar et al. . |
| 4,834,271 | 5/1989 | Litwin . |
| 4,883,483 | 11/1989 | Lindmayer . |
| 4,915,687 | 4/1990 | Sivert . |
| 4,917,669 | 4/1990 | Bonaldo . |
| 4,935,010 | 6/1990 | Cox et al. . |
| 4,950,260 | 8/1990 | Bonaldo . |
| 5,006,114 | 4/1991 | Rogers et al. . |
| 5,065,783 | 11/1991 | Ogle, II . |
| 5,070,885 | 12/1991 | Bonaldo . |
| 5,108,376 | 4/1992 | Bonaldo . |
| 5,122,123 | 6/1992 | Vaillancourt . |
| 5,139,483 | 8/1992 | Ryan . |
| 5,147,333 | 9/1992 | Raines . |

(List continued on next page.)

FOREIGN PATENT DOCUMENTS 9311828  6/1993  WIPO .

Primary Examiner—Kevin Lee
Attorney, Agent, or Firm—Brown, Martin, Haller & McClain

[57] ABSTRACT

A needless valve is described which avoids the suctioning problems of the prior needleless devices upon deactivation and which preferably provides a positive self-purging effect. The valve is self-purging at the end of an administration cycle, avoiding clogging of attached catheters or other devices, and ensures that substantially all of liquid received into the valve is delivered to the receiver. The valve is also extremely simple in design and easy to construct and assemble, since it consists of only three pieces. The valve has a base with a connector for fluid communication attachment to tubing or other device, a solid elongated fluid channeling rod, and an internal fluid flow conduit; a flexible hollow expandable and contractible plug fitting over and moveable along the rod; and a tubular housing fitting over the plug and attached to the base. When the valve is activated by insertion of a nozzle of a fluid source, the rod and plug wall cooperate so that as the plug retracts along the rod, it is stretched and its interior expanded. Upon deactivation, the plug contracts, the interior volume decreases, and the resiling plug wall forces residual fliud within the valve to be expelled through the outlet, purging the residual fluid from the valve. No negative pressure is formed, so no suctioning of blood or other fluid from a patient or receiver occurs.

16 Claims, 3 Drawing Sheets

U.S. PATENT DOCUMENTS

| | | |
|---|---|---|
| 5,154,703 | 10/1992 | Bonaldo . |
| 5,199,948 | 4/1993 | McPhee . |
| 5,201,725 | 4/1993 | Kling . |
| 5,203,775 | 4/1993 | Frank et al. . |
| 5,215,537 | 6/1993 | Lynn et al. . |
| 5,215,538 | 6/1993 | Larkin . |
| 5,242,393 | 9/1993 | Brimnall et al. . |
| 5,251,873 | 10/1993 | Atkinson et al. . |
| 5,269,771 | 12/1993 | Thomas et al. . |
| 5,273,533 | 12/1993 | Bonaldo . |
| 5,279,571 | 1/1994 | Larkin . |
| 5,281,206 | 1/1994 | Lopez . |
| 5,284,475 | 2/1994 | Mackal . |
| 5,295,657 | 3/1994 | Atkinson . |
| 5,306,243 | 4/1994 | Bonaldo . |
| 5,330,450 | 7/1994 | Lopez . |
| 5,344,414 | 9/1994 | Lopez et al. . |
| 5,360,413 | 11/1994 | Leason et al. . |
| 5,370,636 | 12/1994 | Von Witzleben . |
| 5,380,306 | 1/1995 | Brinon . |
| 5,385,372 | 1/1995 | Utterberg . |
| 5,390,898 | 2/1995 | Smedley et al. . |
| 5,395,348 | 3/1995 | Ryan . |
| 5,400,500 | 3/1995 | Behnke et al. . |
| 5,401,245 | 3/1995 | Haining . |
| 5,402,982 | 4/1995 | Atkinson et al. . |
| 5,405,331 | 4/1995 | Behnke et al. . |
| 5,411,499 | 5/1995 | Dudar et al. . |
| 5,417,673 | 5/1995 | Gordon . |
| 5,423,791 | 6/1995 | Bartlett . |
| 5,425,465 | 6/1995 | Healy . |
| 5,433,330 | 7/1995 | Yatsko et al. . |
| 5,439,451 | 8/1995 | Collinson et al. . |
| 5,441,487 | 8/1995 | Vedder . |
| 5,456,668 | 10/1995 | Ogle, II . |
| 5,456,675 | 10/1995 | Wolbring et al. . |
| 5,464,399 | 11/1995 | Boettger . |
| 5,470,319 | 11/1995 | Mayer . |
| 5,470,327 | 11/1995 | Helgren et al. . |
| 5,474,536 | 12/1995 | Bonaldo . |
| 5,480,393 | 1/1996 | Bommarito . |
| 5,501,426 | 3/1996 | Atkinson et al. . |
| 5,518,026 | 5/1996 | Benjey . |
| 5,520,665 | 5/1996 | Fleetwood . |
| 5,533,708 | 7/1996 | Atkinson et al. . |
| 5,533,983 | 7/1996 | Haining . |
| 5,540,661 | 7/1996 | Tomisaka et al. . |
| 5,549,577 | 8/1996 | Siegel et al. . |
| 5,549,651 | 8/1996 | Lynn . |
| 5,552,118 | 9/1996 | Mayer . |
| 5,555,908 | 9/1996 | Edwards et al. ................ 251/149.6 X |
| 5,569,235 | 10/1996 | Ross et al. . |
| 5,573,516 | 11/1996 | Tyner . |
| 5,597,536 | 1/1997 | Mayer . |
| 5,616,130 | 4/1997 | Mayer . |
| 5,674,206 | 10/1997 | Allton et al. . |
| B1 5,251,873 | 10/1993 | Atkinson et al. . |

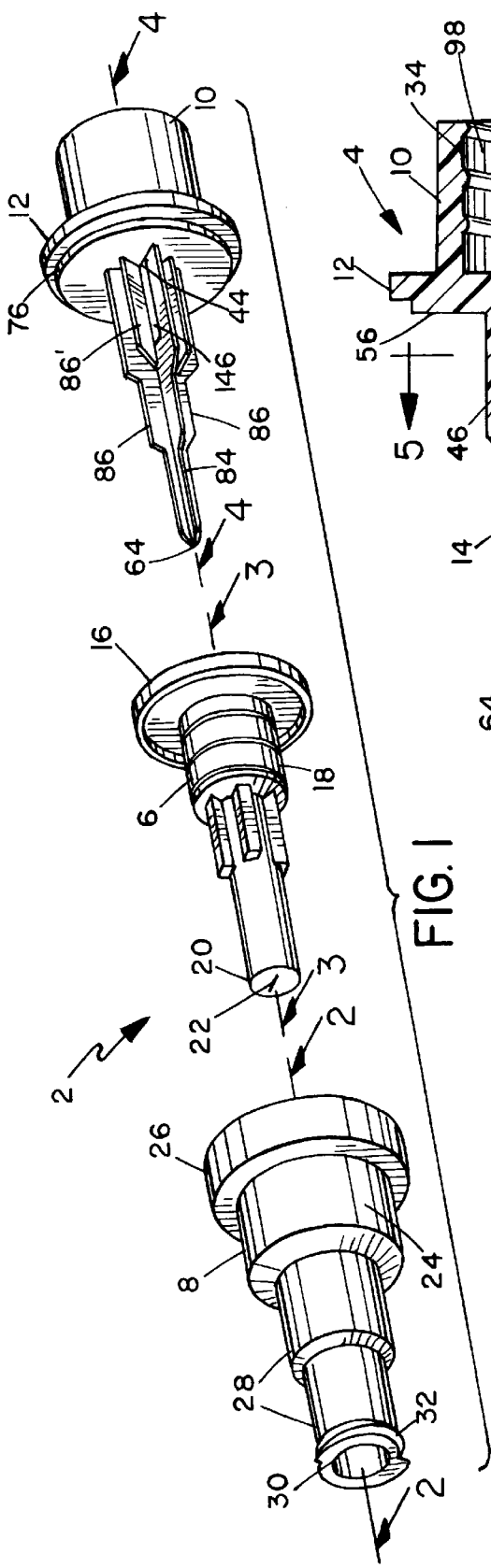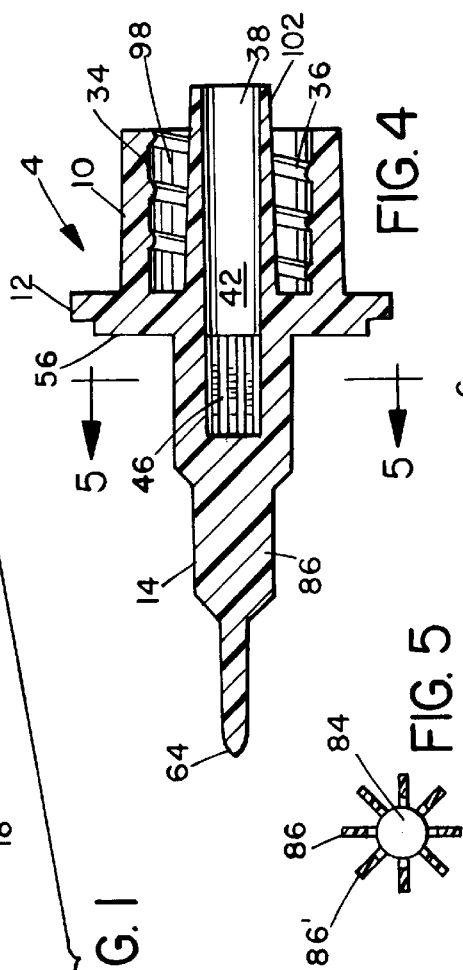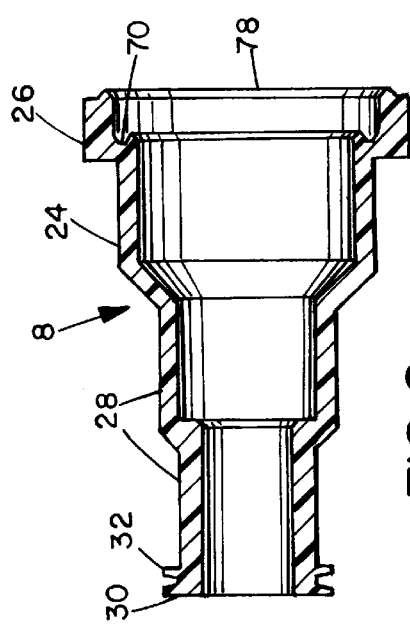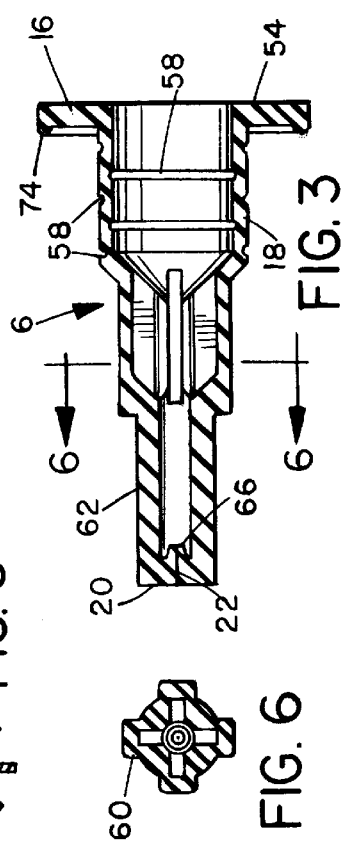

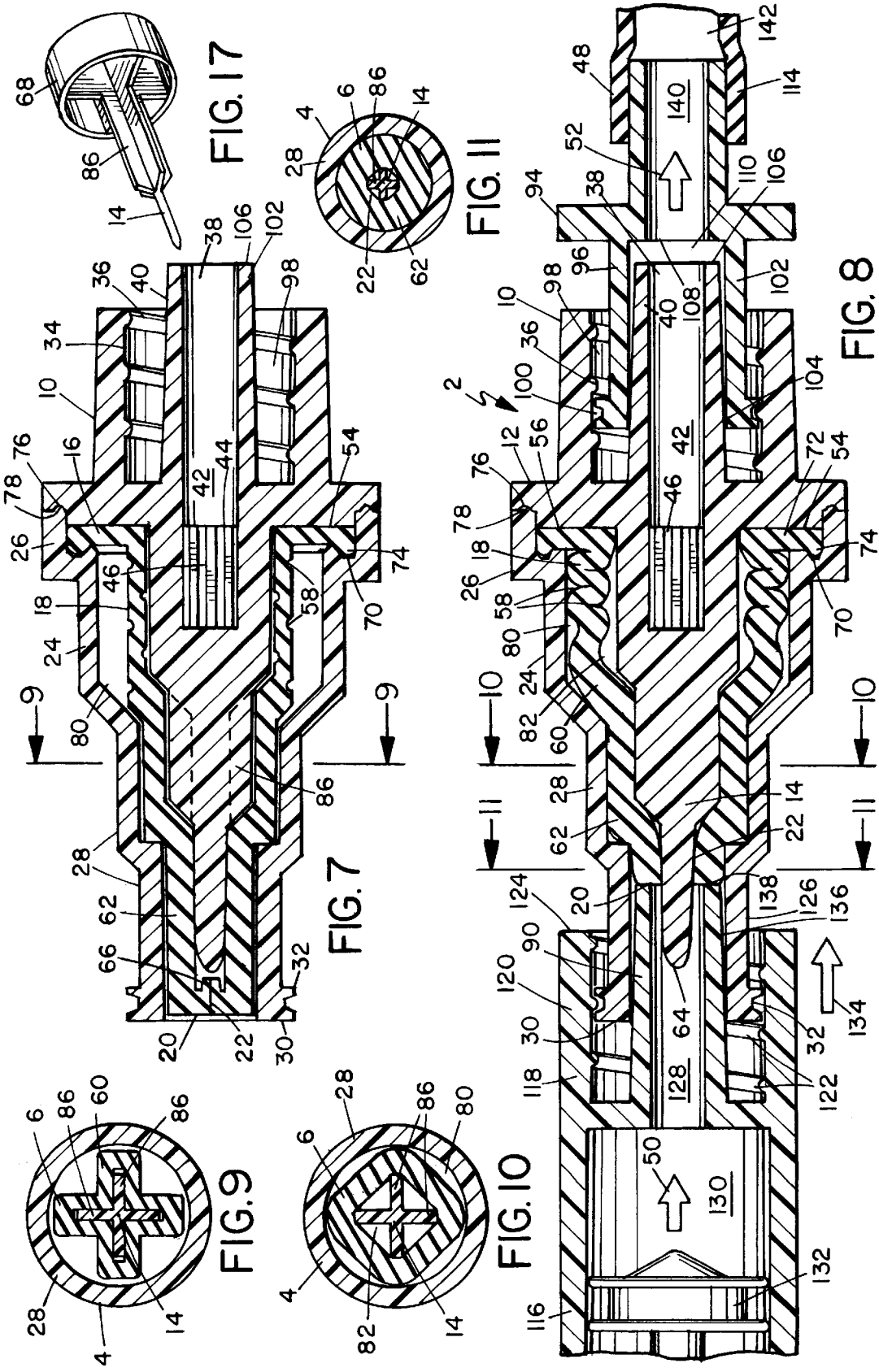

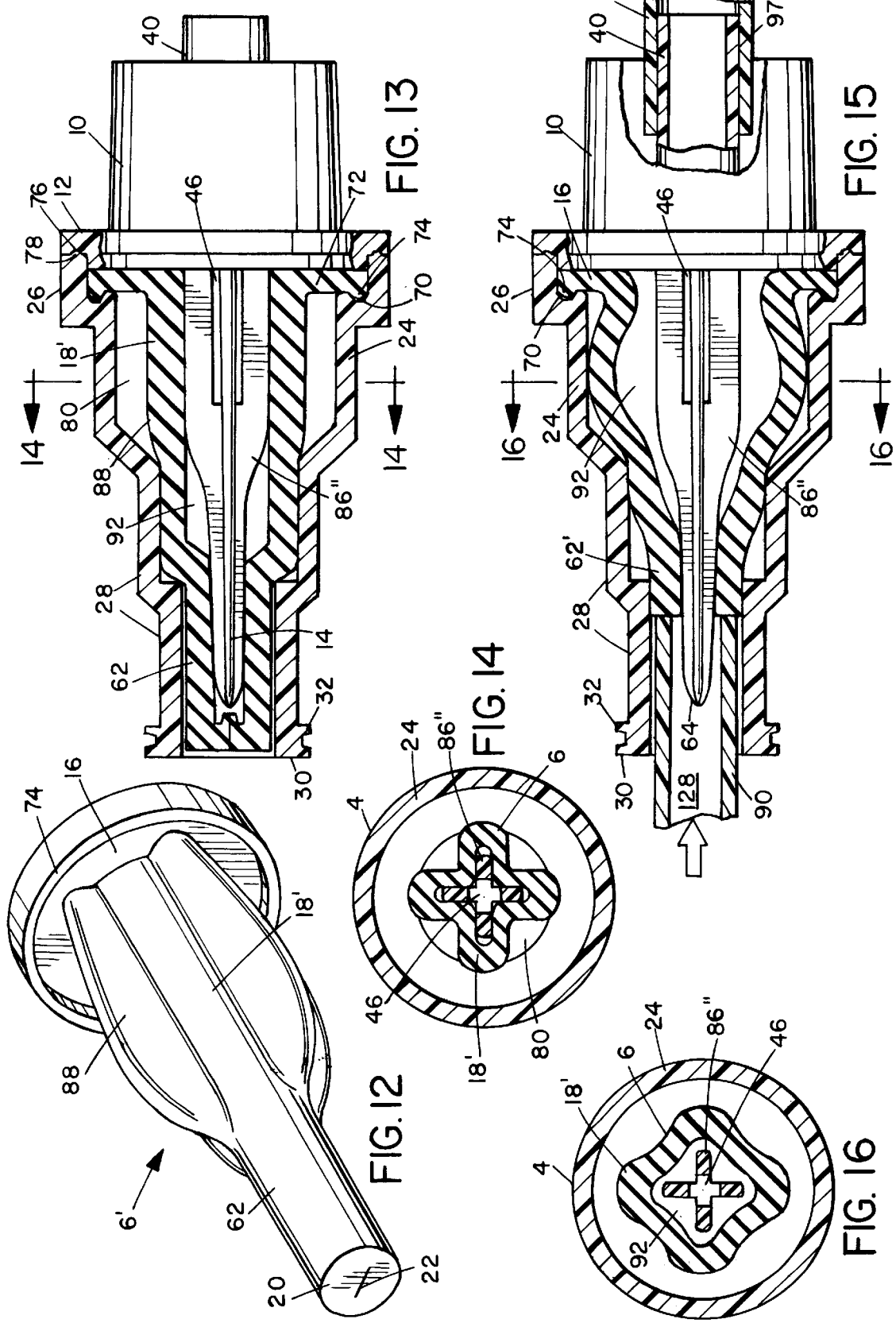

# NEEDLELESS VALVE

BACKGROUND OF THE INVENTION

1. Field of the Invention

The invention herein relates to valves and connectors, such as those use in medical liquid flow applications such as intravenous (IV) administration of medications. More particularly it relates to needleless valves for such applications.

2. Description of the Prior Art

There are many instances, particularly in the medical field, where quantities of liquid must be moved from a source of the liquid to a liquid conduit system under restricted and usually sterile conditions. A principal example is the administration of medication or other liquids to a patient intravenously. When the intravenous administration is to be conducted at periodic intervals over a extended period of time, the conventional practice is to insert a catheter into the patient's vein, usually through the patient's forearm, and leave the catheter in place with a portion extending out of the patient's arm and terminating in a valve (receiver) for periodic connection to the liquid source as required. The presence of the valve avoids the necessity of using direct injection of the patient each time the medication is to be administered, which would be both painful to the patient and also increase the risk of infection each time the skin was penetrated.

For many years, receivers of valves were constructed with a resealable membrane, such as a rubber or other elastomeric plug, stretched across the inlet end of the device, closing off the IV fluid conduit. When it was time to administer medication or other fluid, the physician or nurse would use a conventional hypodermic syringe with a sterile hypodermic needle which would penetrate the rubber plug and allow sterile injection of the fluid in the syringe directly into the liquid conduit or cannula. Upon withdrawal of the hypodermic needle, the elastic rubber plug would resile and seal itself, maintaining the sterile condition of the interior of the system.

Such practice, however, has numerous disadvantages. Repeated piercing of the plug with the hypodermic needles eventually damages the plug sufficiently that it cannot maintain the appropriate sterile seal. Further, since the valve/receiver devices are normally quite small, the plug is even smaller, often less than ¼ inch (6 mm) in diameter. Therefore the person administering the medication had to take care in manipulating the syringe so that the hypodermic needle would pierce the rubber plug and not hit the other portions of the receiver, the patient's arm, or even the hands or arms of the person himself or herself. To take the appropriate amount of care, of course, required some period of time, thus reducing the number of patients a physician or nurse could serve in a given time period. In addition, it was not uncommon for hypodermic needles to break off in the plug during or before administration of the liquid, thus usually becoming lodged in the rubber plug and requiring the administrator to take time to remove the broken needle. Further, such breakage also commonly caused the loss of all or a portion of the medication or other liquid in the syringe and, of course, not properly administered to the patient.

Such problems were particularly common in situations where the medical personnel were required to act very rapidly, such as in emergency room and emergency medical administration settings.

The accidental piercing of the skin of the doctor or nurse raised critical problems. If such occurred before administration of the medication to the patient, the medication, or at least a portion of it, was injected into the nurse or doctor, which not only deprived the patient of the medication, but in fact might be quite harmful to the physician or nurse. If the accident occurred after administration of the fluid to the patient, the hypodermic needle could easily be contaminated by the patient's blood or other bodily fluid, thus being capable of transmitting the patient's disease to the physician or nurse. While this was a severe problem at any time, it became a truly critical problem as various highly infectious or virulent diseases became more prevalent in the population. The added presence of infectious diseases with extremely high rates of mortality among patients, such as AIDS, gave priority to development of devices which would eliminate the need for use of hypodermic needles.

In more recent years, "needleless" connectors and receptors have been developed and widely marketed. In systems using this type of device, the fluid dispenser (usually a syringe) is fitted with a blunt nozzle rather than a hypodermic needle. The blunt nozzle is designed to be received into a corresponding receiver attached to the IV line or other fluid conduit. Within the receiver is normally a hollow tubular cannula, which is a fixed member forming the extended end of the fluid conduit extending into the patient's veins. Sterility of the receivers is important so that transfer of the liquid from the syringe to the cannula and IV fluid conduit can be conducted under sterile conditions.

While the "needleless" concept has been well known and is quite simple, implementation of the concept in practice has been quite difficult. Needleless connectors have, for the most part, been designed with a hollow flexible plug which fits over the cannula and which has a self-sealing slit or similar closeable opening in its exterior end. The interior end of the plug is anchored adjacent to the downstream end of the cannula (i.e. the end leading into the IV system and the patient's arm). Since the cannula is made as a rigid elongated tube, as the nozzle of the fluid dispensing device is pushed into the receiver, it contacts that exterior end of the rubber plug and forces that end inwardly against the distal end of the cannula. The distal end of the cannula contacts the slit at the end of the plug and forces the slit open, so that the plug then becomes a sleeve as it is pushed inwardly along the outer surface of the cannula. Eventually, the distal end of the cannula, now being exposed, contacts the interior fluid transfer tube of the dispensing device as the nozzle of the dispensing device moves further into the receiver. When this connection is made, the fluid can be transferred from the syringe directly into the cannula through which it flows onto the IV system in the patient's body. Such opening of the device is commonly referred to as "activation" of the "valve."

Once the fluid is fully transferred, the nozzle of the dispensing device is withdrawn outwardly through the receiver, causing the flexible plug to resile and extend distally along the cannula until it passes the cannula end and returns to its "deactivated" position enclosing the end of the cannula with the slit again sealed. Examples of devices of this type are shown in U.S. Pat. Nos. 5,065,783 (Ogle) and 5,549,577 (Siegel et al.) and in published PCT application no. WO 93/11828 (Lopez).

While such devices have worked well for the most part, they have been found to have some serious deficiencies. One of the most important is the fact that upon deactivation and withdrawal of the nozzle of the syringe or other fluid dispensing device, the compressed plug resiles back to its original position, thus increasing its internal volume back to its deactivated volume, thus creating a partial vacuum in the cannula and attached catheter. This produces a suctioning effect which often causes the patient's venous blood to be drawn into the catheter where it remains and can clot, thus preventing flow through the catheter. When it comes time to administer the next fluid dose, the plugged catheter prevents administration of the fluid. Remedying of the problem requires that the catheter be cleaned or replaced. This, of course, is a major problem in emergency situations, whether in an emergency room or when a patient on IV suffers some sort of relapse or seizure or other critical condition and medication must be administered through the IV without delay. Even in the absence of an emergency, however, withdrawal of the device for cleaning of the catheter requires that the IV subsequently be reinserted into the patient. In ordinary situations this at least requires the time of a nurse and is a discomfort for the patient. In many cases, however, reinsertion is a problem that requires a doctor's intervention, as for instance where an new acceptable insertion site is difficult to find or the patient does not tolerate needle insertions well. Thus reinsertion presents a significant cost event for the medical team and subsequently for the patient.

Other forms of connectors in needleless couplings have been described. These may have components within the coupling intended to hold the fluid flow conduit open against the tendency of flexible sleeves attached to one or the other end of a coupled tubing to compress and close the fluid flow path. A typical example is shown in U.S. Pat. No. 4,457,749 (Bellotti et al.) in which a "spike" having a cruciform cross section is used to hold open a fluid path within the coupling as the two portions of the tubing are joined together.

SUMMARY OF THE INVENTION

I have now invented a needless valve which avoids the suctioning problems of the prior needleless devices and which, in fact, can be structured to provide a positive self-purging effect upon deactivation. This device retains all of the favorable aspects of the needleless valve system for activation and administering the medication to the patient, but avoids all of the detrimental effects of the prior art devices that occur during deactivation. The present device is virtually impossible to clog, is self-purging at the end of an administration cycle, and helps ensure that substantially all of the medication dispensed from the syringe is administered into the patient. The device is also extremely simple in design and easy to construct and assemble, since it consists of only three pieces. The device may be made in a variety of different configurations, all of which provide the same self-purging action and clear flow path for the administered liquid.

The device of this invention is configured so that a core rod forces the plug to expand during activation in a manner not possible with the prior art devices, which causes the interior volume of the plug to increase substantially from its rest (deactivated) volume and opens a flow path through the valve for the administered fluid. Upon deactivation, the plug resiles and its interior volume returns to rest volume, closing the fluid flow path and displacing residual fluid within the valve, so that the residual fluid is expelled from the valve through its outlet into the downstream conduit or unit, purging the valve and promoting use of all of the administered fluid. In addition, such volume decrease prevents occurrence of any partial vacuum in the valve, and in fact usually creates a transient overpressure, which also assists in purging the valve of residual fluid. The structure thus maintains either a positive or neutral (i.e., non-negative) pressure at all times, preventing any suctioning of blood from a patient into an attached catheter, thus avoiding clogging of the catheter by formation of clots in blood drawn into it.

In a broad embodiment, the invention involves a needleless valve comprising a tubular housing having a fluid inlet end and a fluid outlet end, a solid rod within the housing, and a hollow flexible plug within the housing and moveable along the rod, the hollow plug in response to insertion of a fluid supply nozzle into the inlet end moving in one direction along and cooperating with the rod to increase the volume of the interior of the plug and open a fluid flow path between the inlet and outlet ends, and in response to withdrawal of the fluid supply nozzle from the inlet end moving in an opposite direction along and cooperating with the rod to decrease the volume of the plug interior, close the fluid flow path between the inlet and outlet ends and cause residual fluid in the flow path to be expelled from the valve through the outlet end.

In another broad embodiments, the invention involves a needleless valve having a distal end and a proximal end, and comprising a base disposed at the proximal end and comprising a connector for fluid communication attachment to a fluid flow tube, a solid elongated fluid channeling rod extending from a proximal end joined to the base to a distal end, and a fluid flow conduit formed in the base and extending through the connector into the proximal end the rod and disposed for the fluid communication with the tube; a flexible plug having a wall forming a hollow interior bounded by an inward facing surface; the plug fitting over the rod, being sealingly attached to the base and being moveable along the rod between a first activated position and a second deactivated position; in the first activated position the rod maintaining the plug in a form with the interior having a first larger volume, with the plug withdrawn from the distal end of the rod, and creating a fluid flow path through the interior and along the rod; and in the second deactivated position the plug being in a form with the interior having a second smaller volume with the distal end of the rod covered by the plug and the fluid flow path being blocked by the wall of the plug; and a tubular housing fitting over the plug and extending from the distal end of the device to the base, at the distal end the housing having an elongated receiver for releasable fluid communication reception of a nozzle of a fluid source, the receiver configured to guide movement of the nozzle along the receiver into contact with the plug, the plug moving between the first and the second positions in response to movement of and contact from the nozzle; such that movement of the plug from the first position to the second position in response to insertion of the nozzle into the receiver causing the rod and the plug to cooperate to expand the plug and increase the interior volume and open the valve to fluid flow between the source and the tube, and subsequent movement of the plug from the second position to the first position in response to withdrawal of the nozzle from the receiver causing the plug to resile and the interior volume to decrease, closing the valve to the fluid flow, displacing residual fluid within the valve and causing the residual fluid to flow from the proximal end of the valve into the tube.

In another embodiment the invention also comprises a rod for a needleless valve comprising a solid elongated core having a plurality of coaxial ribs extending outwardly therefrom.

Ribs made be made with a uniform width so that their extended edges are straight, with continuously varying widths so that their edged form straight or curved smooth tapers, or have discontinuously varying widths, so that their edges form one or more steps over the length of each rib. In one embodiment, the ribs terminate at the distal end of the rod in a hollow annular member encircling the rod.

Additional features of the invention as well as descriptions of the various forms of the components will be set forth below.

BRIEF DESCRIPTION OF THE DRAWINGS

FIG. 1 is a perspective view of the device of this invention, with the individual components thereof shown in separated relationship;

FIG. 2 is an enlarged sectional view taken on Line 2—2 of FIG. 1;

FIG. 3 is an enlarged sectional view taken on Line 3—3 of FIG. 1;

FIG. 4 is an enlarged sectional view taken on Line 4—4 of FIG. 1;

FIG. 5 is a sectional view taken on Line 5—5 of FIG. 4;

FIG. 6 is a sectional view taken on Line 6—6 of FIG. 3;

FIG. 7 is a sectional view with the components of FIGS. 2, 3 and 4 shown in assembled relationship;

FIG. 8 is a view similar to FIG. 7, with the valve opened by attachment of a typical Luer-Lok connector;

FIG. 9 is a sectional view taken on Line 9—9 of FIG. 7;

FIG. 10 is a sectional view taken on Line 10—10 of FIG. 8;

FIG. 11 is a sectional view taken on Line 11—11 of FIG. 8;

FIG. 12 is a perspective view of an alternative embodiment of flexible valve component;

FIG. 13 is a sectional view similar to FIG. 7 showing the alternative valve component in closed position;

FIG. 14 is a sectional view taken on Line 14—14 of FIG. 13;

FIG. 15 is a view similar to FIG. 13 showing the valve component opened by insertion of a Luer connector; and FIG. 16 is a sectional view taken on Line 16—16 of FIG. 15.

FIG. 17 is a perspective view illustrating another embodiment of a central rod of the present invention.

DETAILED DESCRIPTION AND PREFERRED EMBODIMENTS

The device is best understood by reference to the drawings. For the purposes of description herein, the following conventions of direction will be maintained. The terms "upstream" and "downstream" will be with respect to the normal direction of fluid flow during administration of medication or other liquid through the valve of the present invention to a patient or other receiver. This is indicated in FIG. 8 by the flow arrows 50 (upstream) and 52 (downstream). Similarly, the terms "distal" and "proximal" will be used with respect to the patient or other receiver, such that the upstream end of the device is also sometimes referred to as the distal end, while the downstream end is also sometimes referred to as the proximal end.

One embodiment of the overall device 2 is shown in FIG. 1, separated into three components: a base 4, plug 6 and housing 8. The principal features of each of the parts may also be seen in FIG. 1. The base 4 consists of a connector 10 which connects the device with the fluid flow tubing or conduit 48, usually through a separate connector 94, as illustrated in FIG. 8; a radial flange 12, which serves as a seat for attachment of the plug 6; and an elongated rod 14 which, as will be described below, cooperates with the plug 6 to provide the unique and desirable operating features of the present invention.

The plug 6 has a seating gasket 16, a compressible mid-section 18 which usually folds into a configuration similar to a bellows, and, at the distal end 20, has a closeable slit or similar opening 22. The housing 8 has a wide diameter expansion portion 24, a coupling ring 26 which, during assembly, is bonded to the flange 12 to retain the device as a single unit and a receiving portion 28, the distal end 30 of which can be configured as shown with threads 32 to join with corresponding threads of a liquid dispenser to couple the two together.

FIGS. 2, 3 and 4 show respectively the housing 8, plug 6 and base 4 in cross-section to facilitate understanding of their operations and functions. Considering first FIG. 4, the base 4 is formed of the aforementioned coupler 10, flange 12 and rod 14. As will be seen from FIG. 4, the coupler 10 is has an annular form with its inner wall 34 formed into threads or ribs 36 to allow it to be attached to a corresponding threaded end of coupler such as 94 as will be described below. Centrally disposed within the annular shaped coupler 10 is a hollow tapered cylinder 40 which has fluid flow channel 38 extending through it. Cylinder 40 is an extension of the flange 12 and rod 14 so that it will be desirable for the entire base unit to be molded as a single piece of rigid material, commonly plastic but also possibly of metal. The fluid flow conduit 38 continues as conduit 42 through the center of flange 12 and terminates as a conduit 46 within the proximal end 44 of rod 14. Fluid flowing downstream along rod 14 from the liquid dispenser 116 during activation of the device 2 thus enters the fluid conduit 46 through the openings 146, flows through aperture conduit 42 through flange 12, and on through the channel 38 into coupler 94 and eventually into tubing 48 as shown in FIG. 8. The extension of cylinder 40 beyond the proximal end of the base 10 facilitates insertion into the coupler 94 or (in the absence of such a coupler) directly into, for example, tubing 48. Tubing 48 may be substituted for by other devices to which the valve is to be attached, such as direct coupling to a storage, test or reaction vessel or to a measuring instrument.

A preferred embodiment of a plug 6 is shown in FIG. 3. The plug 6 is made out of a flexible material, usually a rubber or a polymeric elastomer. In the embodiment shown the plug has a flange 16 which has a flat base 54 to allow it to seat against the corresponding flat distal face 56 of the flange 12 on the base 10, as shown in FIGS. 7 and 8. The most proximal section 18 may be scored with groves 58 on the interior and exterior to permit bellowing or other folding of the section as the plug is compressed and moved posteriorly during activation, as best illustrated in FIG. 8. (Another embodiment of the plug 6 will be discussed below, which has a different form of section 18.) In other embodiments the flange 12 may be eliminated and other means, such as a gripping or adhesive-coated surface (not shown) provided to which the proximal end of plug 6 is secured.

In the preferred embodiment shown in the drawings, the plug 6 also has an intermediate section 60 which can be expanded, but which does not normally flex, fold or compress as extensively as section 18. Both the expansion and compression of section 18 and the expansion of section 60 contribute to the self-purging action of the device 2 as will be described below. The distal portion 62 of the plug 6 extends outwardly just past the tip 64 of rod 14 and normally has a somewhat thicker wall than do sections 18 and 60 to accommodate the opening and subsequent closing of slit 22 in the distal end 20 and to resist buckling of the end 20 when the unit is deactivated. Preferably the slit 22 will be terminated on the interior side of the plug 10 by a "duck bill" flange 66 which assists in causing the slit 22 to resist leakage when internal pressure is present during deactivation.

The housing 8 is a simple rigid shell of plastic or metal, which is intended to fit over the plug 6 and attach to flange 12, thus locking gasket 16 in position, as best shown in FIGS. 7 and 8. The inner portion of coupling ring 26 of housing 8 is configured with a generally semi-circular channel 70 incorporated within it, both of which are configured to accommodate the corresponding base 72 and lip 74 of gasket 16. When the connecting ring 26 is seated against the flange 12 of base 4, preferably aligned by groove 76 into which rib 78 fits, and the two are sealed together as by a conventional adhesive or by heat, ultrasonic or RF welding, the flange 16 of the plug 6 is firmly held against the flange 12 so that the plug cannot be displaced, and also to provide a firm base for subsequent return or resiling of the plug 6 upon deactivation.

The interior of section 24 of the housing 8 is configured to have a substantially greater diameter than the deactivated rest diameter of section 18 of the plug 6, as indicated in FIG. 7, creating an annular space 80 into which the portion 18 can expand as it is compressed to form the generally bellowed configuration shown in FIG. 8.

The rod 14 can have a number of different configurations, all of which are intended to cause the plug 6 to expand outwardly during activation, thus creating the expansion of the elastic plug and increase of its interior volume, so that the plug 6 upon deactivation will return or resile inwardly, decreasing its interior volume and thereby purging fluid from the fluid flow space 82 along the rod 14. The rod 14 can be generally described as having a solid core 84 which terminates in a blunt or rounded tip 64 and which has extending radially outwardly therefrom a plurality of ribs 86 (and perhaps also 86'). The ribs 86 may have various configurations which will cause the plug to expand and which will prevent prolapsing of the plug during activation. For instance, in various embodiments, an elongated rib may be uniform width over most of its length (with preferably a transition curve or slope at its distal end, to facilitate movement of the end 20 of plug 6 along the rod and rib), or it may have a continuously varying width, so that it has a straight or curved tapered profile, or it may have widths that vary discontinuously along its length, so that it has a stepped profile. It is preferred that for ribs in which the widths vary, either continuously or discontinuously, the widths increase from distal to proximal ends, so that no recess or shoulder is formed upon which a portion of the interior of the plug wall could become snagged, preventing or impeding return or resiling of the plug upon deactivation. In yet another alternative, shown in FIG. 17, the proximal ends of the ribs 86 may terminate in a hollow annular member 68 which serves to maintain the maximum expansion of the plug 6 during activation. Conveniently this annular member 68 will be circular, but polygonal shapes are also usable, although polygons of less than six, and probably less than eight, sides should probably be avoided, since they may be unduly angular and tend to impede resiling of the plug upon deactivation.

There may be any convenient number of ribs and they may be disposed at any desired orientation to each other around the circumference of the rod 14. However, normally there will need to be at least three ribs 86, preferably equally spaced at 120° from each other, in order to ensure that the elastic plug 6 is stretched to form a space 82 of appropriate volume. Typically there will be four ribs 86 in a cruciform shape as indicated in FIGS. 9 and 10; although a larger number of ribs, such as eight as shown in FIG. 5, may also be used. It is also possible, and usually preferred, to have different numbers and lengths of ribs on the same rod 14, as illustrated in FIGS. 1 and 5, where the added ribs 86' are interspersed between the principal cruciform ribs 86 but are foreshortened in axial length and extend distally only as far as the length of the widest section of each rib 86. The added ribs help support the extended plug wall and prevent prolapse of unsupported portions of the wall and expansion increases and the wall thickness is thinned by stretching. Given the small size of the device and the desire to maximize the flow channels, it is considered that eight to ten ribs are probably the maximum practical number, with four, six or eight ribs being preferred, and other numbers (both between three and ten and greater than ten) being possible. Use of an even number of ribs as shown in the illustrations is preferred since it is easier to mold symmetrical ribs equally spaced than to mold an asymmetric configuration as would be present with and odd number of ribs. Further, the number of width steps may be two or three as shown or may be more, although again the small size of the device acts as a practical limitation on the number of width steps of the ribs 86 which are either feasible or desirable.

An alternative embodiment of the plug 6 is shown as 6' in FIGS. 12–16. In this embodiment, the plug 6' is configured with an expanded downstream section 18' which substantially replaces sections 18 and 60 in the configuration described above. The section 18' may be somewhat bulbous or it may approximately conform to the shape of the rod 14 (shown in these Figures with an alternative form of the ribs designated as 86"), with the plug 6' having conforming hollow ribs 88. The operation of this alternative plug 6' is illustrated in FIGS. 13 and 15. In the deactivated state, shown in FIG. 13, the plug is essentially in the shape shown in FIGS. 12 and 14. Upon activation by the nozzle 90 of a liquid dispenser, the bulbous section 18' with ribs 88 expands outwardly (as shown in FIGS. 15 and 16) into space 80 and leaves an enlarged open space 92 between the rod 14 and the interior wall surface of the plug 6'. Upon deactivation the plug 6' resiles or is caused to return to the configuration shown in FIG. 13.

It will be evident to those skilled in the art that there are, of course, other configurations of the plug 6 other than that of 6', which will provide equivalent expansion of the plug and increase of its interior volume during activation, and guide the subsequent resiling of the plug and decrease of its interior volume to produce the unique self-purging effect present in the claimed device. It is intended that all such configurations are to be considered within the scope of this invention as defined in the appended claims.

The operation of the invention can best be understood by reference to FIGS. 8, 10 and 11. In a typical application, device 2 is attached to a Luer-Lok™ coupler 94. Coupler 94 is formed with a hollow cylindrical connector 96 which extends into the recess 98 inside coupler 10 and which is secured therein by threads 100 cooperating with ribs or threads 36 on the interior of the coupler 10. In the embodiment shown, cylinder 40 has a tapered outer surface 102 which causes a wedging action with the interior of connector 96 as indicated at 104, such that as the connector 94 is turned and threaded into the recess 98 the cylinder 40 and connector 96 are tightly wedged together sealing against any loss of fluid. Alternatively both cylinder 40 and connector 96 can be straight with parallel surfaces, and they can be secured together by an adhesive, such as a solvent adhesive, as shown at 97 in FIG. 15.

Preferably the design of the tapered cylinder 40 and connector 96 are such that the end 106 of cylinder 40 and the opposing surface 108 on the interior of connector 96 are closely adjacent or abutting such that the space 110 between them is minimized.

Connection of the device of this invention to tubing 48 or any other device may be configured to be releasable or permanent, as desired. In the embodiment shown, the connector has at its opposite end a nipple 112 to which the conventional tubing 48 is attached. The tubing is normally stretched slightly as indicated at 114 so that the tubing 48 is retained on the nipple 112 by the combination of the elastic resiliency of the tubing and the interference fit between the inner surface of the tubing 48 and the outer surface of the nipple 112. If there is concern that the tubing 48 may separate from the nipple 112, a conventional external clamp (not shown) may be placed around the circumference of the tubing 48 where it overlaps the nipple 112 and tightened to ensure good connection between the tubing and the nipple. Alternatively various adhesives or solvents may be used to secure the tubing and nipple together. The solvents or adhesives must be selected such that they do not intrude into the fluid flow path of the device or migrate to cause unwanted adhesion elsewhere in the device.

Activation and deactivation of the valve 2 will be best understood by comparison of FIG. 7 and 8. The device in its deactivated configuration is shown in FIG. 7, with the plug 6 in its "rest" or fully resiled orientation. (For purposes of comparison, it will be understood that connector 94 and tubing 49 of FIG. 8 should be imagined also to be present in FIG. 7.) Activation comprises joining of the needleless valve 2 to a liquid supply source such as a syringe or other reservoir device, partially shown at 116 in FIG. 8. Connection is usually through a coupler 118 which is similar in configuration to the coupler 10 of the valve. Coupler 118 consists of an outer cylindrical wall 120 which has on its inner side ribs or threads 122. Aligned with the center axis of coupler 118 is nozzle 90 which extends outwardly from the end 124 of coupler 118 and which is tapered to fit into the receiving portion 126 of section 28 of the housing 8. The interior of nozzle 90 is an open fluid flow channel 128 which is in fluid communication with the interior 130 of liquid reservoir 116. The reservoir 116 is here illustrated as a conventional syringe device, with a movable piston 132 housed within a cylinder 130. The piston 132 is manipulated by the physician or nurse as indicated by the arrow 50 to force the liquid forward. Such use and operation of the fluid dispensing device 116 are conventional and need not be described further. Similarly, such devices may take many different forms, all of which are equally applicable to the present invention.

As the coupler 118 is moved forward (as indicated by the arrow 134) by interaction of the threads 32 and 112, the tapered nozzle 90 interacts with the inner surface 136 of the receiver section 126 of the housing to create a wedging action similar to that described above between the connectors 94 and 10, thus forming a mechanically tight connection. Simultaneously the front end 138 of coupler 118 comes into contact with distal end surface 20 of plug 6 and forces the plug 6 to compress in the downstream or proximal direction, thus causing the slit 22 to contact the tip 64 of rod 14 and be forced open as it passes over and around the tip 64, as best illustrated in FIG. 11. The compressive movement of the rest of the plug 6 caused by the forward motion of the nozzle 90 causes the other portions of the plug 6 to move along corresponding sections of the rod 14 and ribs 86 (and 86', if present), thus forcing the wall of the plug 6 to be stretched and expanded outwardly, substantially increasing the interior volume of the plug 6 and creating the space 82 through which the fluid can flow along the surfaces of rod 14 and ribs 86. With the plug 6 thus retracted, the liquid can flow freely from the liquid reservoir or supply device 116 through the nozzle 90 and the now-opened slit 22, along and adjacent to the outer surfaces of the rod 14 and ribs 86 (through the elongated V-shaped spaces 82 formed by adjacent ribs 86, the rod 14, and the inner surface of the plug 6, and on through the openings 146 and into the conduits 46, 42 and 38, on through the channel 140 in the nipple 112 and into the interior 142 of tubing 48, and subsequently to the patient or other receiver.

Because the liquid source 116 and the valve 2 are securely locked together by the interaction of threads 32 and 112 and the wedging action of the receiver 126 and nozzle 90, this activated configuration is stable and can be maintained for as long as the physician, nurse or other user wishes to continue dispensing the liquid. It can also, of course, be maintained for an extended period of time without human supervision or control, where the reservoir or liquid supply device 116 is mechanically or electrically operated and provides a continuous or intermittent flow of fluid through the valve 2 to the patient or receiver.

In prior art devices, the flexible plug merely slid along the outside of the tubular cannula. Since the cannula had a uniform diameter, the plug remained strongly compressed over substantially all of its length, being stretched or expanded only at the distal tip, and then only by the minimal amount necessary to open the end slit and allow the end of the hollow cannula to protrude into the nozzle of the fluid dispensing device. As the nozzle of the dispensing device was subsequently withdrawn and the plug allowed to resile back in the distal direction along the outer surface of the cannula and closed over the open end of the cannula, a partial vacuum was created in the cannula. This in turn commonly resulted in liquid being withdrawn from the patient or receiver and pulled by suction back into the catheter to which the cannula of the prior art device was connected. Where the receiver was a human patient, the fluid drawn back into the cannula would usually consist in whole or in part of venous blood. The blood thus retained in the cannula would thereafter often congeal and coagulate, causing blockage of the hollow interior cannula and making subsequent administration of fluid difficult or impossible until the valve and cannula were either replaced or cleaned.

FIG. 8 illustrates the improvement of the present invention in which such creation of partial vacuum is entirely avoided and the self-purging property of the device is illustrated. The plug, by being stretched to increase the interior volume during activation, resiles and decreases that volume during deactivation, so that the contraction of the plug wall into the space 82 (essentially eliminating space 82) displaces substantially all residual fluid remaining within the valve upon deactivation, and forces it to be expelled through the exit conduits. In addition, the resiling of the plug wall often creates a transient overpressure which also assists in expulsion of the residual fluid. Since the plug ultimately resiles back to its rest configuration the overpressure decreases to neutral pressure. Because the center member of this device is solid rod 14 rather than an open cannula, the end 20 of resiling plug 6 passes over distal end 64 of rod 14 and slit 22 closes before the decrease in interior volume, and therefore purging action of the resiling plug, is completed. Consequently, unlike in the prior art valves, no negative pressure is formed by the movement of end 20 and the closing of slit 22.

The self-purging and pressure-creating operation of the device is evident from FIG. 8. As the nozzle 90 is withdrawn from the receiver, section 18 of plug 6 which has been under compression and has been stretched and expanded over the ribs 86 of the rod 14, begins to resile and return toward the configuration shown in FIG. 7. This causes the space 82 to be closed, completely or substantially, and all fluid which has been in that space is thus forced through openings 146 into conduit 46 and on through to conduits 42, 38, 140 and 142 and into the receiver or patient, leaving no significant amount of fluid remaining in the valve, as will be evident by comparison of FIGS. 9 and 10. This is the exact opposite of the operation the prior art devices, where return of the plug to the deactivated position has no effect on the interior volume of the cannula, since the cannula is made of a rigid plastic or similar material and therefore is not deformed by pressure from the plug. Thus the liquid remaining in the interior of the cannula cannot be purged by the return of the plug to its deactivated position. In the present invention, by contrast, the resiling or return of the plug to its deactivated position forces the remaining fluid in the valve downstream to the receiver or patient.

In most cases, the return and closing action of the plug 6 (or 6') will be adequately accomplished entirely by the resiliency of the elastic material forming the plug, such that no outside biasing or urging of the plug is necessary. However, if desired, one could supplement the normal resiliency of plug 6 by, during assembly of the device, filling the space 80 with an inert gas 144 such as nitrogen or argon, preferably under pressure. Thus, as the device is activated and the wall of the plug 6 is forced to expand outwardly by the rod 14 and ribs 86, it encounters the compressed gas within the space 80 and, while reducing the volume of space 80, compresses (or further compresses) the gas 144. Consequently, when the device is deactivated, the compressed gas 144 acts on the outside surface of the plug 6 and as the volume of chamber 80 begins to increase (and space 82 decrease), the pressure of the expanding gas supplements the normal resiliency of the plug 6 material, causing the device to purge itself more quickly and completely. The expanding compressed gas 144 forces the plug material to assume the configuration shown in FIG. 9 more completely, with closer fitting between the interior wall of the plug 6 and the exterior surface of the rod 14 and ribs 86. The same effect will be seen by comparison of FIGS. 14 and 16 for the embodiment of the rib 6' shown in FIG. 12, involving spaces 80 and 92. (One could also achieve the same effect by mechanical rather than pneumatic action if one were to emplace small springs (not shown) within space 82 and in contact with the outer surface of the plug wall and the inner surface of the housing wall, and which would be compressed when the plug 6 expanded. Upon deactivation, the compressed would then resile and expand, urging the plug wall inward and assisting in decreasing the interior volume of the plug.

It will thus be seen that, unlike prior art devices in which the fluid flow channel through the valve has a fixed volume within a cannula, the device of the present invention with its variable volume flow path formed by the interaction of the center rod and ribs and the expanding and contracting interior dimension of the plug, employs a unique self-purging and pressure generating action that causes essentially all of the fluid to be forced into the receiver or patient. This not only keeps the valve from being clogged by return flow of blood or other receiver fluid, but also ensures that substantially all of the dosage of the fluid intended for the patient or receiver is, in fact, administered, with no signficant amounts retained or lost within the valve structure itself.

For brevity, the device and its operation have been described herein in terms of administration of IV fluid or similar medications to a human patient. However, it will be evident that this valve also has numerous other uses in related medical areas, such as administration of medications or nutrients through the gastrointestinal system of a patient. It also has many uses outside the medical field, such as administration of small quantities of liquid reactants or reagents in chemical or biological or medical testing procedures, or in the precise administration and delivery of chemical reactants in processes to produce small quantities of specialty chemicals. Other uses may include precise delivery of standard fluids for calibration of test instruments or for conducting hydraulic or other fluid flow experiments or small scale production processes.

It will be evident to those skilled in the art that there are numerous embodiments of the present invention which, while not expressly described above, are clearly within the scope and spirit of the invention. The above description is therefore intended to be exemplary only and the scope of the invention is to be determined solely from the appended claims.

I claim:

1. A needleless valve comprising a tubular housing having a fluid inlet end and a fluid outlet end, a solid rod disposed between said fluid inlet end and said fluid outlet end within said housing and having expander means extending therefrom, and a hollow flexible plug within said housing overlying said rod and moveable therealong away from said fluid inlet end in response to insertion of a fluid supply nozzle into said inlet end and toward said fluid inlet end in response to withdrawal of said fluid supply nozzle from said inlet end, said hollow plug cooperating with said expander means of said rod to increase the volume of the interior of said plug during movement away from said fluid inlet end and cooperating with said expander means of said rod to decrease the volume of said plug interior during movement toward said fluid inlet end, whereby a fluid flow path between said inlet and outlet ends is alternately opened and closed and upon closing of said flow path residual fluid therein is expelled from said valve through said outlet end.

2. A needleless valve as in claim 1 further comprising said rod being elongated coaxially of said valve and said expander means comprising a plurality of longitudinal ribs extending outwardly therefrom, said ribs cooperating with said plug in said increase in said interior volume and in said decrease in said interior volume.

3. A needleless valve as in claim 2 wherein the distance a rib extends outwardly from said core varies over the length of said rib.

4. A needleless valve as in claim 3 wherein the distances of outward extent of said rib varies continuously over the length of said rib.

5. A needleless valve as in claim 3 wherein the distances of outward extent of said rib varies discontinuously over the length of said rib.

6. A needleless valve as in claim 2 further comprising said ribs terminating adjacent said outlet end in a hollow annular member encircling said rod.

7. A needleless valve having a distal end and a proximal end, and comprising:
a base disposed at said proximal end and comprising a connector for fluid communication attachment to a fluid flow tube, a solid elongated fluid channeling rod extending from a proximal end joined to said base to a distal end, and a fluid flow conduit formed in said base and extending through said connector into said proximal end of said rod and disposed for said fluid communication with said tube;
a flexible plug having a wall forming a hollow interior bounded by an inward facing surface; said plug fitting over said rod, being sealingly attached to said base and being moveable along said rod between a first activated position and a second deactivated position; in said first activated position said rod maintaining said plug in a form with said interior having a first larger volume, with said plug withdrawn from said distal end of said rod, and creating a fluid flow path through said interior and along said rod; and in said second deactivated position said plug being in a form with said interior having a second smaller volume with said distal end of said rod covered by said plug and said fluid flow path being blocked by said wall of said plug; and a tubular housing fitting over said plug and extending from said distal end of said valve to said base, at said distal end said housing having an elongated receiver for releasable fluid communication reception of a nozzle of a fluid source, said receiver configured to guide movement of said nozzle along said receiver into contact with said plug, said plug moving between said first and said second positions in response to movement of and contact from said nozzle;

such that movement of said plug from said first position to said second position in response to insertion of said nozzle into said receiver causing said rod and said plug to cooperate to expand said plug and increase said interior volume and open said valve to fluid flow between said source and said tube, and subsequent movement of said plug from said second position to said first position in response to withdrawal of said nozzle from said receiver causing said plug to resile and said interior volume to decrease, closing said valve to said fluid flow, displacing residual fluid within said valve and causing said residual fluid to flow from the proximal end of said valve into said tube.

8. A needleless valve as in claim 7 further comprising said rod being elongated coaxially of said valve and having a plurality of longitudinal ribs extending outwardly therefrom, said ribs cooperating with said plug in said increase in said interior volume and in said decrease in said interior volume.

9. A needleless valve as in claim 8 wherein the distance a rib extends outwardly from said core varies over the length of said rib.

10. A needleless valve as in claim 9 wherein the distances of outward extent of said rib varies continuously over the length of said rib.

11. A needleless valve as in claim 9 wherein the distances of outward extent of said rib varies discontinuously over the length of said rib.

12. A needleless valve as in claim 8 further comprising said ribs terminating adjacent said outlet end in a hollow annular member encircling said rod.

13. A needleless valve as in claim 7 wherein said cooperation between said rod and said plug as said plug interior decreases in volume creates a transient positive pressure against residual fluid enhancing said expulsion of said fluid from said valve into said tube.

14. A needleless valve as in claim 7 wherein said flexible plug is formed of a resilient material.

15. A needleless valve as in claim 7 further comprising an interior surface of said housing adjacent said proximal end forming a chamber surrounding said rod and a portion of said plug, said chamber being filled with gas, such that said expansion of said plug into said chamber causes compression of said gas, said compressed gas thereafter acting to enhance resiling of said plug and decrease of said interior volume.

16. A needleless valve as in claim 7 wherein said plug comprises an expanded proximal section which upon activation enhances the degree of expansion of said interior volume.

* * * * *

UNITED STATES PATENT AND TRADEMARK OFFICE
CERTIFICATE OF CORRECTION

PATENT NO.    : 6,029,946
DATED         : February 29, 2000
INVENTOR(S)   : Mark Christopher Doyle Page 1 of 1

It is certified that error appears in the above-identified patent and that said Letters Patent is hereby corrected as shown below:

Title page,
"U.S. PATENT DOCUMENTS" add the following patents:
-- 5,616,129    4/1997      Mayer
5,685,866       11/1997     Lopez
5,820,601       10/1998     Mayer
5,873,862       2/1999      Lopez --.

Column 4,
Line 61, delete "made" first occurrence, replace with -- may --.

Signed and Sealed this

Fifteenth Day of January, 2002

Attest:

JAMES E. ROGAN
Attesting Officer    Director of the United States Patent and Trademark Office